(12) United States Patent
Chemat et al.

(10) Patent No.: US 11,202,973 B2
(45) Date of Patent: Dec. 21, 2021

(54) METHOD FOR EXTRACTING WATER-SOLUBLE COMPOUNDS FROM MICROALGAE AND/OR CYANOBACTERIA

(71) Applicants: ALGAMA, Evry (FR); UNIVERSITÉ D'AVIGNON ET DES PAYS DE VAUCLUSE, Avignon (FR)

(72) Inventors: Farid Chemat, Morieres-les-Avignon (FR); Maryline Abert Vian, Aramon (FR); Léa Vernes, Le Pontet (FR); Thomas Felice, Clamart (FR); Mathieu Goncalves Alves, Paris-9E-Arrondissement (FR)

(73) Assignees: ALGAMA, Evry (FR); UNIVERSITÉ D'AVIGNON ET DES PAYS DE VAUCLUSE, Avignon (FR)

( * ) Notice: Subject to any disclaimer, the term of this patent is extended or adjusted under 35 U.S.C. 154(b) by 64 days.

(21) Appl. No.: 16/618,640

(22) PCT Filed: Jun. 15, 2018

(86) PCT No.: PCT/FR2018/000172
§ 371 (c)(1),
(2) Date: Dec. 2, 2019

(87) PCT Pub. No.: WO2018/229364
PCT Pub. Date: Dec. 20, 2018

(65) Prior Publication Data
US 2021/0146275 A1    May 20, 2021

(30) Foreign Application Priority Data
Jun. 15, 2017 (FR) .................... 1770630

(51) Int. Cl.
*B01D 11/02* (2006.01)
*A61K 36/02* (2006.01)
(Continued)

(52) U.S. Cl.
CPC .......... *B01D 11/0265* (2013.01); *A61K 36/02* (2013.01); *B01D 11/0484* (2013.01);
(Continued)

(58) Field of Classification Search
CPC ................ A61K 31/40; A61K 2236/00; A61K 2236/30; A61K 2236/37; A61K 36/02;
(Continued)

(56) References Cited

FOREIGN PATENT DOCUMENTS

| CN | 104844707 | * | 8/2015 | ........... C07K 14/795 |
| CN | 105820237 | * | 8/2016 | ........... C07K 14/795 |

OTHER PUBLICATIONS

CN104844707, Method for extracting phycocyanobilin from spirulina, English Translaiton, 5 pages (Year: 2015).*
(Continued)

*Primary Examiner* — Yate' K Cutliff
(74) *Attorney, Agent, or Firm* — Birch, Stewart, Kolasch & Birch, LLP

(57) ABSTRACT

The present invention relates to the field of upgrading biomass, in particular algal biomass, and more specifically the present invention relates to a method for extracting water-soluble compounds from microalgae and/or cyanobacteria, as well as the product obtained by this method and the uses of same, in particular in the food industry or as food supplements.

20 Claims, 1 Drawing Sheet

(51) Int. Cl.
  *B01D 11/04*     (2006.01)
  *B01D 21/26*     (2006.01)

(52) U.S. Cl.
  CPC ........ *B01D 21/262* (2013.01); *A61K 2236/30* (2013.01); *A61K 2236/37* (2013.01); *B01D 2259/816* (2013.01)

(58) Field of Classification Search
  CPC .............. A61K 35/748; B01D 11/0265; B01D 21/262; B01D 11/0484; B01D 2259/816; C07D 201/44; C07K 1/145
  See application file for complete search history.

(56) References Cited

OTHER PUBLICATIONS

CN105820237, Method for two aqueous phase extraction separation of phycocyanin through dextran and sodium potassium tartrate, English translation 9 pages (Year: 2016).*

Gerde, J.A., et al., Evaluation of microalgae cell disruption of ultrasonic treatment, Bioresource Technology, vol. 125, pp. 175-181 (Year: 2012).*

Hadiyanto, H., et al., Response surface optimizaiton of ultra sound assisted extraction (UAE) of phycocyanin from microalgae Spirulina platensis, Emirates Journal of Food and Agricultural, 28(4), pp. 227-234 (Year: 2016).*

* cited by examiner

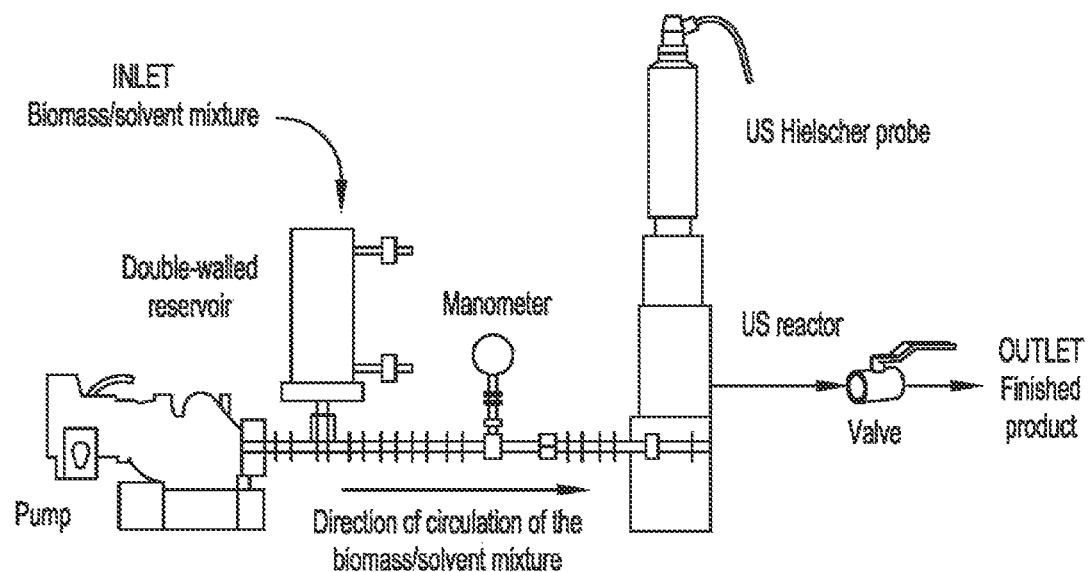

METHOD FOR EXTRACTING WATER-SOLUBLE COMPOUNDS FROM MICROALGAE AND/OR CYANOBACTERIA

BRIEF DESCRIPTION OF THE DRAWINGS

The FIGURE is a diagram of the mano-thermo-sonication (MTS) mounting device for the implementation of the method according to the invention.

DETAILED DESCRIPTION OF THE PREFERRED EMBODIMENTS

The present invention relates to the field of upgrading biomass, in particular algal biomass, more specifically the present invention relates to a method for extracting water-soluble compounds from microalgae and/or cyanobacteria, as well as the product obtained by this method and the uses of same, in particular in the food industry or as food supplements.

In order to cope with the increase of global food demand, many manufacturers are orienting towards alternative resources, such as microalgae. These microorganisms, of a large biodiversity, represent a unique biomass source. The production thereof is distinguished from that of horticultural plants and cereal crops, grown on arable land, by the very high surface yield thereof.

Grown for more than 30 years, microalgae constitute a whole food product. In human and animal nutrition, two upgrading approaches exist: the first consists of aiming for a whole microalgae consumption, the second relates to the extraction, the transformation and the conditioning of bio-active molecules coming from these. In France, only three species of microalgae are authorised for a human consumption without transformation and hold exceptional nutritional properties: *Spirulina* or *Arthrospira platensis*, green microalgae *Chlorella* and diatom *Odontella aurita*. These microorganisms are proclaimed as major elements in the challenge of global food supply, thanks to the unique content thereof in proteins and the low environmental impact of the production thereof: low water and energy consumption.

In particular, *Spirulina* has thus attracted, over the last few years, the attention of a large number of researchers and manufacturers. It is already very common on the market in the dry, non-transformed form, for the consumption thereof as a food supplement.

*Spirulina* containing a large number of compounds of high added-value interest, many researchers and manufacturers are interested in extracting compounds of interest from this cyanobacteria. The biomolecule usually extracted from *Spirulina* is phycocyanin (PC), antioxidising blue pigmented protein, representing 20% of the dry weight thereof (Vonshak, 1997). This growing interest for phycocyanin is explained, in particular by the tinting strength thereof. Currently, the blue food colourants used in France are synthetic: patent blue V and shiny blue; they appear often among the ingredients of sweets and drinks, etc. Patent blue V would be at the origin of an amplification of hyperactivity in children and could constitute a potential allergen, that is why it has recently been forbidden in the United States, Canada and Australia. Due to this, a particular attention has been brought onto the use of natural colourants, and in particular phycocyanin. Numerous studies are thus based on the extraction of this protein from *Spirulina*. On the scale of the laboratory of the methods such as maceration in different solvents, enzymatic lysis, ultrasounds, are used. Thus, bibliographic studies detail several protocols for extracting PC from *Spirulina*: use of ultrasounds (20 kHz, 200 W) in the phosphate buffer 0.1M and pH 6.8 (Furuki et al, 2003), maceration in the phosphate buffer for 4 hours at ambient temperature under continuous stirring (Chaiklahan et al, 2011), use of Tris-HCl buffer with lysozymes (Wenjun et al, 2013), cold maceration in distilled water for 24 hours (Kamble et al, 2013), maceration in the sodium acetate buffer at 30° C. for 24 hours (Silveira et al, 2007).

In order to produce PC extracts in large quantity, methods for extracting from *Spirulina* have been developed or adapted to the industrial scale. Thus, patents protecting extraction methods are found. For example, patent WO 2014045177 A1 filed in 2013 by Ecosystem protects an extraction method consisting of macerating the *Spirulina* biomass for 15 days in a glycerol then using a dead-end filtration in order to recover the filtrate containing the concentrated PC. However, this method for extracting by maceration has two disadvantages: the duration of extraction and the low yield. Other methods, called "intensification methods", have emerged over the last few years in order to overcome this problem: the use of microwaves, ultrasounds, supercritical fluids (CO2), enzymatic lysis, etc. Supercritical fluids are mainly used to extract hydrophobic, liposoluble compounds such as carotenoids, tocopherols, fatty acids, etc. (Supercritical Carbon Dioxide and Microwave-Assisted Extraction of Functional Lipophilic Compounds from *Arthrospira platensis*, Esquivel-Hernandez et al, 2016). Moreover, several authors report the use of ultrasound for extracting microalgae, and in particular, *Spirulina* (Ultrasound assisted extraction of beta-carotene from *Spirulina platensis*, Dey and Rathod, 2013_Phycocyanin extraction from microalgae *Spirulina platensis* assisted by ultrasound irradiation: effect of time and temperature, Hadiyanto et al, 2016). These techniques called "intensification techniques" have the advantage of being more rapid and effective compared with conventional methods such as maceration. However, conventional ultrasound extraction techniques do not make it possible to obtain an extract of which the composition of water-soluble compounds is modulable according to the nature and the quality desired for each water-soluble compound.

The methods cited above aim to obtain "bonded" *Spirulina* extracts in phycocyanin for uses of natural food colourant or as a food supplement in the form of unit vials. Only a few rare *Spirulina* extracts are, to date, intended to be incorporated to food formulations and are only used to colour them.

In certain other microalgae such as *Chlorella*, which is constituted of cellulose and has a strong rigidity leading to an increased resistance of algae facing mechanical stresses, these methods would not make it possible to effectively extract water-soluble compounds such as chlorophyll.

The Applicants have today developed a method which makes it possible to modulate the cavitation bubbles generated by ultrasounds, at the origin of the effectiveness of the extraction, by other parameters applied during the treatment of microalgae to the ultrasounds, such as pressure, temperature, flow, thus making it possible for an intensification and a modulation of the method for extracting water-soluble compounds, according to the nature and the quantity of the water-soluble compounds desired in the extract.

Contrary to what already exists on the market, the method according to the invention makes it possible to generate, in an optimised manner, on the industrial scale, from a starting microalgae biomass, of an aqueous solution and a method, different extracts with a high nutritional value, rich in water-soluble compounds, in particular proteins, water-soluble vitamins, chlorophyll, phycocyanin and minerals, intended for human food, said extracts having modulable compositions in said water-soluble compounds. According to the parameters of ultrasonic power (Pus), Temperature, Pressure and flow selected at the start, it is thus possible to make the nutritional composition vary from the extract, but also the colour thereof.

Thus, a first aim of the present invention relates to a method for obtaining water-soluble compounds from eukaryotic microalgae (microalgae) or prokaryotes (cyanobacteria), characterised in that said method comprises at least one step of extracting said water-soluble compounds by an ultrasound treatment with use of an ultrasonic power (Pus) of between 10 and 1000 W/L applied to the microalgae or to the cyanobacteria mixed with an aqueous solution to which is applied, preferably concurrently, a pressure (P) of between 1 and 2 bars, a temperature (T) of between 5 and 70° C., and a flow (D) of between 1 and 1000 L/hour.

By microalgae, this means designating, according to the present invention, eukaryotic microalgae, which are characterised by a cellular wall and a nucleus, comprising chlorophytes, chrysophytes and pyrophytes, said eukaryotic microalgae being commonly called "microalgae", and prokaryotic microalgae, which do not have a nucleus and cellular wall, comprising cyanophytes, named below specifically as "cyanobacteria".

Preferably, according to the invention, eukaryotic microalgae are selected from among chlorophytes, preferably from among *Chlorella, Nannocloropsis, Dunaliella* and *Euglena*.

Preferably, according to the invention, cyanobacteria are selected from among *Spirulina* (*Arthrospira platensis* or *Spirulina maxima*) and AFA (*Aphanizemenon Floesaquae*).

Particularly preferably, according to the invention, the microalgae according to the invention is *Spirulina*.

By water-soluble compounds, this means designating, according to the present invention, compounds which are soluble in water and contained in microalgae and/or cyanobacteria, preferably selected from among proteins and peptides, water-soluble vitamins, preferably vitamins of the group B (in particular, Thiamine (B1), Riboflavin (B2), Niacin (B3), Pantothenic acid (B5), pyridoxine (B6), Biotin (B8), Folate (B9), Cobalamin (B12)), minerals, preferably sodium, calcium, potassium, magnesium and iron, C-phycocyanin (or phycocyanin), and chlorophyll.

Particularly preferably, according to the invention, the microalgae according to the invention is *Spirulina* and the water-soluble compound is C-phycocyanin.

By ultrasound treatment with use of an ultrasonic power (Pus), this means designating, according to the present invention, a physical treatment implementing an ultrasound reactor. Preferably, according to the invention, the ultrasonic power is between 10 and 1000 W/L of aqueous solution mixed with microalgae or with cyanobacteria, preferably between 30 and 100 W/L, also preferably between 50 and 80 W/L. Preferably, the energy deployed by the ultrasound reactor varies between 500 and 5000J, the supply flow of the ultrasound reactor varies from 1 L/hour and 1000 L/hour, preferably 1 L/hour, and the ultrasound treatment is carried out for a duration varying from 30 seconds to 90 minutes.

By aqueous solution, this means designating, according to the present invention, an aqueous solution compatible for a food use. Preferably, this means designating a buffered water, preferably phosphate buffer at pH 7, the buffer used being sodium phosphate. In particular, it is preferable that the aqueous solution according to the invention does not comprise any chemical preservatives, or also organic solvents or petrochemical origin (methanol, chloroform, hexane, ethanol) which have a toxicity which would make them incompatible for a food use of the water-soluble compounds obtained by the method according to the invention. It is not desirable either, to use an acid solvent, as certain water-soluble compounds, such as phycocyanin are very sensitive to the pH and any significant variation of the pH, below pH 5 and above pH 7.5 leads to the precipitation thereof. An alcohol solvent is not preferred, as certain water-soluble compounds such as phycocyanin thus lose a large portion of the antioxidant properties thereof.

Preferably, according to the present invention, the microalgae or cyanobacteria/aqueous solution ratio is between 1/5 and 1/50.

Concurrently to this ultrasonic treatment and to this flow is applied a pressure (P) of between 1 and 2 bars, and a temperature (T) of between 5 and 70° C., preferably between 20 and 30° C. Particularly preferably, the temperature is maintained constant between 20 and 30° C. for the whole duration of the method for extracting water-soluble compounds.

Preferably, according to the invention, the microalgae/aqueous solution mixture is collected in a double-walled reservoir. Said reservoir can be thermostatically-controlled, thanks to a water circulation and a thermostat making it possible to adjust the desired temperature. The mixture is then sent using a pump and a valve to an ultrasound reactor comprising an ultrasonic probe connected to an ultrasound generator. Said ultrasound reactor can itself also be preferably equipped with two walls, making it possible to be thermostatically-controlled thanks to a water circulation and a thermostat making it possible to adjust the desired temperature. The valve makes it possible to impose a resistance on the circulation of the mixture and therefore increase the pressure undergone by the mixture. Preferably, a manometer makes it possible to monitor, upstream of the ultrasound reactor, the pressure exerted on the mixture, and to modulate the opening of the valve to apply the desired pressure on the mixture.

Thus, preferably, according to the invention, the temperature (T) is controlled using a thermostat, preferably via a thermostatically-controlled water circulation in the two walls of a reactor comprising the microalgae/aqueous solution mixture, and the mixture is maintained at the desired temperature. It must be noted, that during the ultrasound treatment step, with possibly application of a pressure greater than 1 bar, the temperature of the mixture will tend to increase, and that the thermostat can thus have the role of maintaining a constant temperature of the mixture. Controlling the temperature makes it possible to avoid an increase which is too high, which would risk damaging the heat-sensitive water-soluble compounds, called thermolabile. The Applicant has highlighted that when the temperature exceeds 40° C., certain molecules of interest, such as phycocyanin, can be masked (by chlorophyll, for example). Moreover, the temperature optimal to the extraction of water-soluble compounds of interest are situated around 25° C. Thus, with a thermoregulation at 20° C., coupled with the heating effect of the ultrasounds, a temperature close to 25-30° C. (close to the optimal extraction temperature) is obtained. However, the modulation of the temperature makes it possible to extract different types of compounds: at a low temperature, the extraction of thermolabile compounds is favoured, while at an increased temperature, the heat-sensitive compounds are masked, but other molecules which are more difficult to extract cold are found in solution, such as chlorophyll (of an apolar nature, soluble in organic solvents in normal time).

Preferably, according to the invention, the pressure (P) is applied using a valve on the system making it possible to supply the reactor where Pus will be applied, and makes it possible to impose a resistance to the circulation of the microalgae/aqueous solution mixture in the system. The closer the valve is to the closed position, the more the flow is made difficult, due to the narrowing of the orifice, which causes a slowing down of the circulation of the microalgae/aqueous solution mixture in the system; yet, the pump imposes a constant flow, which causes an increase in pressure.

According to a preferred aspect of the present invention, the ultrasonic power, the pressure, the temperature and the flow are modulated to make the water-soluble compounds extracted from said eukaryotic microalgae or cyanobacteria vary.

Thus, by modulating Pus, T, P and/or D, different extracts can be produced from one same starting microalgae or cyanobacteria biomass, with a given aqueous solution.

Thus, preferably, according to the invention, the higher the ultrasonic power, the pressure and the temperature delivered to the environment are, the richer the extract will be in proteins and in chlorophyll. On the contrary, the lower the ultrasonic power and the temperature are, the less rich the extract will be in water-soluble compounds.

Thus, for example, an ultrasonic power of 100 W/L can be applied with a pressure of 2 bars at a controlled temperature of 20° C. for 10 minutes on a *Spirulina* and phosphate buffer mixture 7 to obtain an extract richer in chlorophyll, and therefore of a more intense green colour than through a method with an ultrasonic power of 30 W/L with a pressure of 1 bar at a controlled temperature of 20° C. for 10 minutes which will be bluer.

Preferably, according to the invention, the duration of the ultrasonic treatment step is between 1 and 90 minutes. The modulation of the duration makes it possible to make the composition vary in water-soluble compounds, and therefore also the concentration. This is explained by the fact that the more the microalgae/aqueous solution mixture passes frequently in the ultrasonic reactor, the more it is going to be subjected to ultrasounds and release water-soluble compounds.

According to a preferred aspect of the present invention, the ultrasonic power, the pressure, and temperature and the flow are modulated to make the colour of the extract obtained vary through said method.

Thus, preferably, according to the invention, the higher the ultrasonic power, the pressure and the temperature delivered to the environment are, the richer the extract will be in proteins and in chlorophyll and therefore the more intense green colour. On the contrary, the lower the ultrasonic power and the temperature are, the less rich the extract will be in water-soluble compounds and the bluer the colour of the extract generated will be (due to the absence of chlorophyll).

According to a preferred aspect of the present invention, the steps are applied to the eukaryotic microalgae or cyanobacteria and aqueous solution mixture continuously, preferably using a pump ensuring the circulation of the mixture in a closed or open circuit.

According to a preferred aspect of the present invention, the method for obtaining water-soluble compounds according to the invention further comprises, an additional step of solid-liquid separation, preferably by centrifugation, of the extract obtained during the extraction step.

According to a preferred aspect of the present invention, the method for obtaining water-soluble compounds according to the invention further comprises an addition step of filtering the liquid portion obtained by separating the solid portion (cell debris) from the extract.

Preferably, according to the present invention, the filtration is carried out in a dead-end manner, advantageously on a food filter, for example made of polyamide, in particular made of nylon, with a fineness of 2 to 50 microns, preferably less than 25 microns.

According to a second extract, the invention relates to the products such as obtained by the method according to the invention containing water-soluble compounds present in the microalgae or cyanobacteria.

More specifically, said method makes it possible to extract the water-soluble compounds from the microalgae and cyanobacteria, separated from the liposoluble fraction of the microalgae or of the cyanobacteria. Preferably, the extract produced will have organoleptic qualities, as well as an optimal nutritional composition.

According to a third aspect, the invention relates to the use of products such as obtained by the method according to the invention in chemical, food, cosmetic or pharmaceutical compositions.

Given the advantages mentioned above presented by these filtrates/extracts, the uses thereof in the food, medical or cosmetic industry, including as food supplements, prove to be particularly useful. The invention also aims for, as new products, the retentates obtained from the filtration step. These retentates can also be used in the food, medical or cosmetic industry, or as food supplements.

An embodiment of the invention will now be described, as a non-limiting example, in reference to the appended schematic drawings, wherein the FIGURE is a diagram of the mano-thermo-sonication (MTS) mounting device for the implementation of the method according to the invention, comprising a probe and an ultrasonic reactor to generate Pus, a thermostat to adjust T, a valve and a manometer to adjust P and a pump to adjust D. The sequencing of the method according to the invention will now be described, as a non-limiting example.

Said method is presented in the form of a closed or open circuit (according to the number of cycles selected), making it possible for the treatment of a microalgae solution (5% in MS) continuously.

Description of the different elements of the MTS mounting:

1) The reservoir makes it possible to receive the microalgae and aqueous solution mixture of be treated. This is a double-walled reservoir which could be thermostatically-controlled thanks to a water circulation.

2) A pump regulates the circulation of the mixture in the system at a constant flow.

3) The ultrasonic probe is connected to a generator, making it possible to fix the desired ultrasonic power. The probe is immersed in the liquid to be treated at ⅔ and emits a fixed frequency which itself is specific (around 20 kHz).

4) The ultrasound reactor is equipped with two walls, making it possible to thermostatically control the mixture via a circulation of thermostatically-controlled water. The ultrasonic probe enters into the reactor, so as to deliver ultrasonic waves in the environment.

5) The valve makes it possible to impose a resistance on the circulation of the mixture and therefore to increase the pressure in the system. It is possible to visually monitor this variation of pressure on the manometer present upstream of the ultrasonic reactor.

Once the mixture is treated with ultrasounds in the continuous device, an emptying of the system is carried out, in order to bring the mixture into a centrifugation module, making it possible for a solid/liquid separation between the solid biomass residues and the water-soluble fraction. A filtration step makes it possible to obtain a clear and transparent extract.

EXAMPLES

Example 1: US Low Power, without Pressure->Blue Extract

The biomass (*Arthrospira platensis*) is mixed with an aqueous solution of extraction (phosphate buffer pH 7) according to the ratio 1/20; that is 1 g of biomass for 20 g of aqueous solution. In this case, 4 g of *Spirulina* is introduced into 80 mL of aqueous solution. The mixture is subjected to low ultrasonic power ultrasounds (30 W) for 10 minutes, with a thermoregulation at 20° C. No pressure is imposed on the system. The extracts are then centrifuged for 10 minutes at 8000 rpm, then filtered by dead-end filtration on Büchner (porosity 8 µm), in order to remove possible suspended particles.

The extract obtained is of a blue colour, due to the presence of phycocyanin (8.34 g/100 g Dry Matter (MS)) and contains 33.36 g/100 g MS of proteins.

Example 2: US High Power+Pressure->Green, Protein-Rich Extract

The biomass (*Arthrospira platensis*) is mixed with an aqueous solution of extraction (phosphate buffer pH 7) according to the ratio 1/20; that is 1 g of biomass for 20 g of aqueous solution. In this case, 4 g of *Spirulina* is introduced into 80 mL of aqueous solution. The mixture is subjected to ultrasonic power ultrasounds (100 W/L, that is around 80% of amplitude) for 10 minutes, with a thermoregulation at 20° C. and a pressure close to 2 bars. The extracts are then centrifuged for 10 minutes at 8000 rpm, then filtered by dead-end filtration on Büchner (porosity 8 µm), in order to remove possible suspended particles.

The extract obtained is of an intense green colour, due to the presence of chlorophyll which has been extracted due to the intensity of the method. Phycocyanin is still present in the extract (11.47 g/100 g MS) and the protein content is 46.19%.

The invention claimed is:

1. A method for obtaining water-soluble compounds from eukaryotic or prokaryotic microalgae, said method comprising at least one step of extracting said water-soluble compounds by an ultrasound treatment with application of an ultrasonic power (Pus) comprised between 10 and 1000 W/L applied to the eukaryotic or prokaryotic microalgae mixed with an aqueous solution, to which is applied, concurrently, a pressure (P) of between 1 and 2 bars, a temperature (T) of between 5 and 70° C., and a flow (D) of between 1 and 1000 L/hour.

2. The method according to claim 1, wherein the ultrasonic power, the pressure, the temperature and the flow are modulated to make the water-soluble compounds extracted from said eukaryotic or prokaryotic microalgae vary.

3. The method according to claim 1, wherein the duration of the step is between 30 seconds and 90 minutes.

4. The method according to claim 1, wherein the ultrasonic power, the pressure, the temperature and the flow are modulated to make the colour of the extract obtained by said method vary.

5. The method according to claim 1, wherein the steps are applied to the eukaryotic or prokaryotic microalgae and aqueous solution mixture continuously.

6. The method according to claim 1, wherein the extracted water-soluble compounds are selected from among proteins and peptides, water-soluble vitamins, minerals, and chlorophyll.

7. The method according to claim 1, wherein the eukaryotic microalgae are selected from among *Chlorella, Nannocloropsis, Dunaliella* and *Euglena*, and that the prokaryotic microalgae are selected from among *Arthrospira platensis* or *Spirulina maxima* and *Aphanizomenon Floes-aquae*.

8. The method according to claim 1, wherein it comprises an additional solid-liquid separation step of the extract obtained.

9. The method according to claim 8, further comprising an additional step of filtering the liquid portion obtained by separation from the extract.

10. The method according to claim 1, wherein the eukaryotic or prokaryotic microalgae aqueous solution ratio is between 1/5 and 1/50.

11. The method according to claim 2, wherein the duration of the step is between 30 seconds and 90 minutes.

12. The method according to claim 2, wherein the ultrasonic power, the pressure, the temperature and the flow are modulated to make the colour of the extract obtained by said method vary.

13. The method according to claim 3, wherein the ultrasonic power, the pressure, the temperature and the flow are modulated to make the colour of the extract obtained by said method vary.

14. The method according to claim 2, wherein the steps are applied to the eukaryotic or prokaryotic microalgae and aqueous solution mixture continuously.

15. The method according to claim 3, wherein the steps are applied to the eukaryotic or prokaryotic microalgae and aqueous solution mixture continuously.

16. The method according to claim 4, wherein the steps are applied to the eukaryotic or prokaryotic microalgae and aqueous solution mixture continuously.

17. The method according to claim 2, wherein the extracted water-soluble compounds are selected from among proteins and peptides, water-soluble vitamins, minerals, and chlorophyll.

18. The method according to claim 3, wherein the extracted water-soluble compounds are selected from among proteins and peptides, water-soluble vitamins, minerals, and chlorophyll.

19. The method according to claim 1, wherein the steps are applied to the eukaryotic or prokaryotic microalgae and aqueous solution mixture continuously by using a pump ensuring the circulation of the mixture in a closed or open circuit.

20. The method according to claim 1, wherein it comprises an additional solid-liquid separation step by centrifugation of the extract obtained.

* * * * *